US009430613B1

(12) United States Patent
Walton, III

(10) Patent No.: US 9,430,613 B1
(45) Date of Patent: Aug. 30, 2016

(54) SYSTEM AND METHOD FOR PROVIDING ACCESS TO ELECTRONICALLY STORED MEDICAL INFORMATION

(71) Applicant: James F. Walton, III, Tallahassee, FL (US)

(72) Inventor: James F. Walton, III, Tallahassee, FL (US)

(*) Notice: Subject to any disclaimer, the term of this patent is extended or adjusted under 35 U.S.C. 154(b) by 0 days.

(21) Appl. No.: 14/968,985

(22) Filed: Dec. 15, 2015

Related U.S. Application Data

(63) Continuation-in-part of application No. 14/742,205, filed on Jun. 17, 2015, now Pat. No. 9,330,235.

(51) Int. Cl.
G06F 19/00 (2011.01)
(52) U.S. Cl.
CPC .................... G06F 19/322 (2013.01)
(58) Field of Classification Search
USPC ......................................................... 235/375
See application file for complete search history.

(56) References Cited

U.S. PATENT DOCUMENTS

| | | | |
|---|---|---|---|
| 5,658,016 A | 8/1997 | Goeken | |
| D426,833 S | 6/2000 | Vanelli | |
| 6,513,720 B1 | 2/2003 | Armstrong | |
| 6,747,561 B1 | 6/2004 | Reeves | |
| 6,751,805 B1 | 6/2004 | Austion | |
| 6,845,063 B2 | 1/2005 | Mitchell | |
| 6,978,268 B2* | 12/2005 | Thomas | G06Q 10/10 |
| 7,827,043 B2 | 11/2010 | Tahan | |
| 8,180,654 B2* | 5/2012 | Berkman | G06Q 50/22 705/3 |
| 8,602,311 B2* | 12/2013 | Walton, III | G06F 19/323 235/487 |
| 2002/0120470 A1 | 8/2002 | Trice, Sr. | |
| 2003/0058110 A1 | 3/2003 | Rich | |
| 2003/0101077 A1 | 5/2003 | Whol | |
| 2003/0150143 A1 | 8/2003 | Hazard | |
| 2005/0194270 A1 | 9/2005 | Gombar | |
| 2006/0010012 A1 | 1/2006 | Franzblau et al. | |
| 2006/0015368 A1 | 1/2006 | Hockey | |
| 2006/0085226 A1 | 4/2006 | Kamber | |
| 2006/0142057 A1 | 6/2006 | Schuler et al. | |
| 2007/0158411 A1 | 7/2007 | Krieg, Jr. | |
| 2007/0265884 A1 | 11/2007 | Lubell et al. | |
| 2008/0126729 A1 | 5/2008 | Cai et al. | |
| 2008/0319798 A1 | 12/2008 | Kelley | |
| 2009/0076849 A1 | 3/2009 | Diller | |
| 2009/0101721 A1 | 4/2009 | Hawthorne et al. | |
| 2009/0295569 A1 | 12/2009 | Corwin et al. | |
| 2010/0115609 A1 | 5/2010 | Spence | |

* cited by examiner

Primary Examiner — Christle I Marshall
(74) Attorney, Agent, or Firm — Livingston Loeffler, P.A.; Edward M. Livingston, Esq.; Bryan L. Loeffler, Esq.

(57) ABSTRACT

A system and method of providing access to electronically stored medical information that appoints third party care takers as records custodians with access to a group of individuals' medical information remotely and securely via an electronic device so the medical information and/or personal records may be provided to medical providers during a medical emergency, thereby speeding up the process of one or more group members receiving required medical treatment.

19 Claims, 4 Drawing Sheets

SYSTEM AND METHOD FOR PROVIDING ACCESS TO ELECTRONICALLY STORED MEDICAL INFORMATION

CROSS-REFERENCE TO RELATED APPLICATIONS

This application is a continuation-in-part of U.S. patent application Ser. No. 14/742,205 filed on Jun. 17, 2015 which is currently pending. The patent application identified above is incorporated herein by reference in its entirety to provide continuity of disclosure.

FIELD OF THE INVENTION

This invention relates to providing personal medical information to medical service providers and records custodians through the use of machine-readable mediums, electronic devices and/or the Internet wherein a plurality of individuals' medical information and/or personal records are grouped together and one or more custodians are provided access and administrative rights to the group's medical information, medical records and personal records.

BACKGROUND OF THE INVENTION

During a medical emergency and/or when visiting a medical service provider for medical treatment it is important that medical providers be aware of a patient's medical history including allergies to drugs, current medications and medical conditions. It also becomes necessary to have the patient's emergency contact information and physician contact information. Conventional methods of providing such information include the patient writing out or orally providing his or her medical history and/or the medical service provider obtaining the records from the patient's past medical service provider's and physicians.

A problem arises with maintaining the security and privacy of sensitive medical information stored remotely and/or on electronic mediums. It is important to only allow access to such sensitive information to medical service providers and/or individuals who have been confirmed as health care surrogates, caretakers, approved records custodians who are authorized to access an individual's medical records and/or are responsible for the individual.

Such a problem arises when care of a group of individuals is administered by a third party other than a primary caretaker. A third party may be a school administrator, coach, youth leader, and so forth. This problem arises for children in schools, on sports teams, in youth programs, attending camps, on overnight outings or in any other situation where an individual is in a third party's care. This situation may also arise for adults at their place of business, sports clubs, gyms and so forth. In situations such as these, one or more responsible parties or surrogate caretakers must be provided with quick access to group members' medical histories and/or personal records in the event of an emergency.

Other personal records may include consent forms, authorization forms, permission forms and so forth that need to be easily provided by a parent or guardian and easily accessed by a caretaker.

Therefore, a need exists for a system and method of providing access to electronically stored medical information that appoints third party care takers as records custodians with access to a group of individuals' medical information and/or personal records remotely and securely via an electronic device so the medical information may be provided to medical providers during a medical emergency, thereby speeding up the process of one or more group members receiving required medical treatment.

SUMMARY OF THE INVENTION

The primary object of the present invention is to provide a system and method of providing access to electronically stored medical information that appoints third party care takers as records custodians with access to a group of individuals' medical information remotely and securely via an electronic device so the medical information may be provided to medical providers during a medical emergency, thereby speeding up the process of one or more group members receiving required medical treatment.

An additional object of the present invention is to provide a system and method wherein personal records, such as consent forms, authorization forms, permission forms and so forth, are easily provided by a parent or guardian and easily accessed by a caretaker.

The present invention fulfills the above and other objects by providing a system and method of providing access to electronically stored medical information, such as blood type, allergies, medical conditions, present medications, age, doctor information and emergency contact information. The medical information may be accessed directly from a machine-readable medium and/or from a remote database over the Internet wherein medical information for a plurality of individuals is stored in the remote database and grouped together so that one or more authorized records custodians may access any of the group members medical records in the event of a medical emergency to provide to a medical provider. The medical information may be retrieved using an electronic device such as a computer, smart phone or table, via the Internet.

An advantage of the method and system of the present invention is an added layer of security for allowing access to stored medical records and information by requiring records custodians to register with the service provider and be pre-authorized by having their credentials authenticated. After the records custodians have been confirmed and pre-authorized they are allowed to use a downloadable software application from the service provider to access medical records for specific individuals within the group. The records custodians must enter a security code or perform some other security recognition function, such as biometric recognition prior to accessing medical records. This ensures that only preauthorized records custodians are able to access an individual's medical information. This also allows the service provider to track who is accessing an individual's medical information, when the information is accessed and the geographic location of the request.

The software will be used in retrieving medical emergency information for anyone involved in an emergency situation. The software will be available preferably as a free download, and can be used by records custodians as well as medical providers and/or an individual owner of a medical information account or his or her appointed representatives. Records custodians will be verified by a registration process with the service provider that requires them to provide their relevant identifying data and be authorized by the service provider and/or a group records administrator. Once verified for a group, the records custodians will be able to access one or more individual's emergency medical information. At the time of accessing the central database to obtain the individual's medical records, the records custodians can access electronic emergency medical records by inputting identifying information for the individual. The identifying information may be input into the electronic device using a keyboard, voice recognition, a blue-tooth device, touch screen, radio frequency identification ("RFID"), near field communications ("NFC"), biometrics, eye movement, facial recognition, head or body gestures. The emergency medical records will then be delivered to the records custodians and will contain one or more of the following: user profile data (photo, first name, middle name, last name, birthday, gender, blood type, race, primary language, secondary language, address, city, state, zip, height, weight, hair color, eye color, cell phone number, home phone number, work phone number, fax number, phone number, email address, insurance company name, group number, policy number, insurance phone number, organ donor (Yes or No), allow blood transfusions (yes or no), emergency contacts (first name, last name, address, city, state, zip code, cell phone number, work phone number, home phone number, email address, relationship), medications (name, dosage, how often), medical conditions (asthma, COPD, seizure disorder, dementia, Alzheimer's, hyperglycemia, hypoglycemia, diabetes type 1, diabetes type 2, high blood pressure, contact lenses, rheumatic fever, pacemaker, heart stent, fistula and so forth), allergies (name, description, notes/info), physician information (name, address, city, state, zip code, phone number, email address, specialty). The records custodians requesting the medical information is then documented with regard to his or her name, date and time of access, and GPS location when the information is requested.

The system and method also allows personal records, such as consent forms, authorization forms, permission forms and so forth, to be easily provided by a parent or guardian and easily accessed by a caretaker. For example, such forms may be electronically signed by a parent and then saved in the database to be reviewed and/or accessed at alter time by a group records administrator. Physical copies of signed forms may also be digitized and then saved in the database.

A group records administrator may include but is not limited to a school employee, coach, youth leader, camp employee, employer or any other third party caretaker. A records custodian may be referred to separately or fall within the definition of a group records administrator.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which.

DESCRIPTION OF THE PREFERRED EMBODIMENTS

Figure 1:
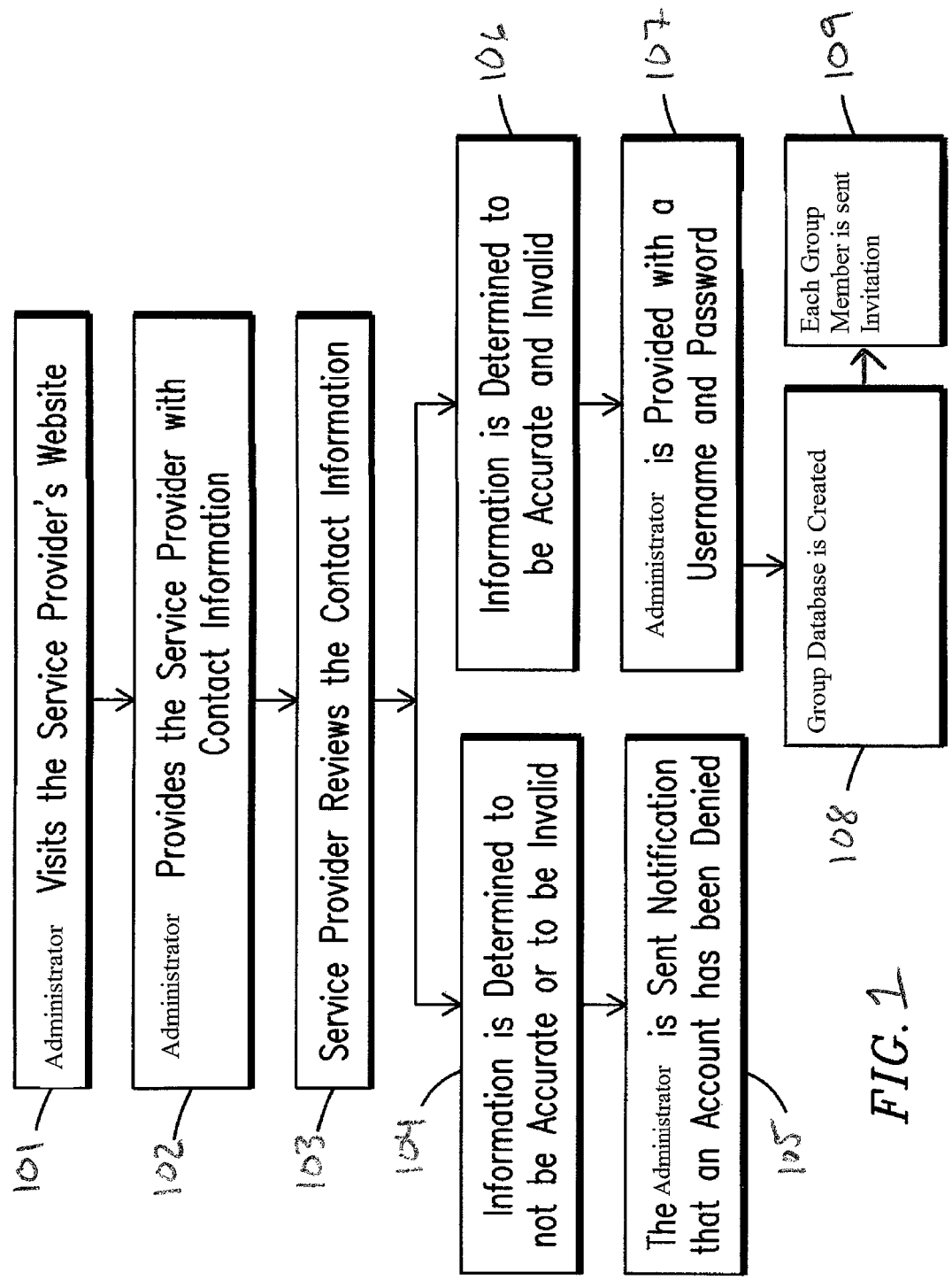
FIG. 1 is a flow chart showing a group record administrator signing up for an account with a service provider and a group database being created.

With reference to FIG. 1, a flow chart showing a group records administrator signing up for an account with a service provider and a group database being created; is illustrated. First, the group records administrator visits the service provider's website 101. Then, the group records administrator provides the service provider with his or her contact information, which includes the individual's name, address, phone number, email address, payment information and so forth and/or the similar contact information for the group records administrator's organization 102. The service provider then reviews the contact information to determine the accuracy of the information and the validity of the information 103. If the information is determined to not be accurate or to be invalid 104, then the group records administrator is sent notification, preferably via email, that the account has been denied 105. If the information is determined to be accurate and valid 106, then the group records administrator is sent an approval, preferably via email, that an account has been created and the group records administrator is provided with a username and password 107. Next, the a group database is created 108 and individuals in the group are sent invitations to join the group by logging into the service provider's website using a preferably temporary username and password and providing additional information 109 (as described in FIG. 2).

Figure 2:
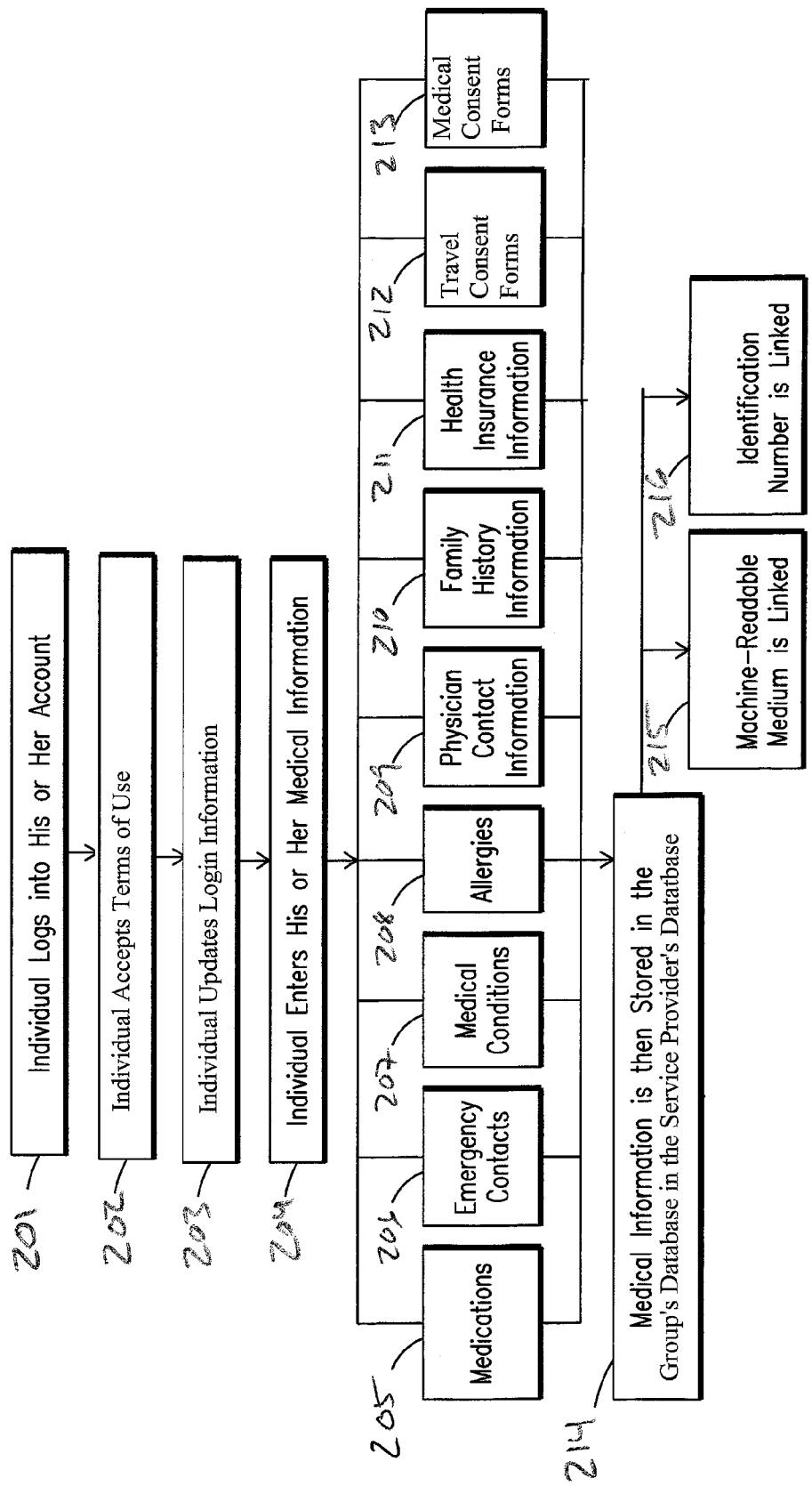
FIG. 2 is a flow chart showing the system and method of the present invention in which an individual joins the group and enters medical information into the group database.

With reference to FIG. 2, a flow chart showing the system and method of the present invention in which an individual joins the group and enters medical information into the group database is illustrated. First, the individual logs into his or her account using the username and password provided by the service provider 201. Then, the individual accepts terms of use, privacy policy and HIPAA Compliance policy 202. Next, the individual may be required to change his or her username and password in compliance with HIPAA policy 203. Then, the individual enters his or her medical information 204, which may include but is not limited to medications 205, emergency contacts 206, medical conditions 207, allergies 208, physician contact information 209, family history information 210, health insurance information 211, travel consent forms 212, medical consent forms 213 and so forth. The medical information is then stored in the group's database in the service provider's central database 214. One or more machine readable mediums may then be assigned to the individual group member's personal medical information within the group database 215. The machine readable medium may be a barcode, QR code and so forth. One or unique identifiers may also then be assigned to the individual's or group member's personal medical information within the group database 216. The unique identifier may be a driver's license number, student identification number, government issued identification or other unique identifier that is pre-existing or created especially for the individual group member.

Figure 3:
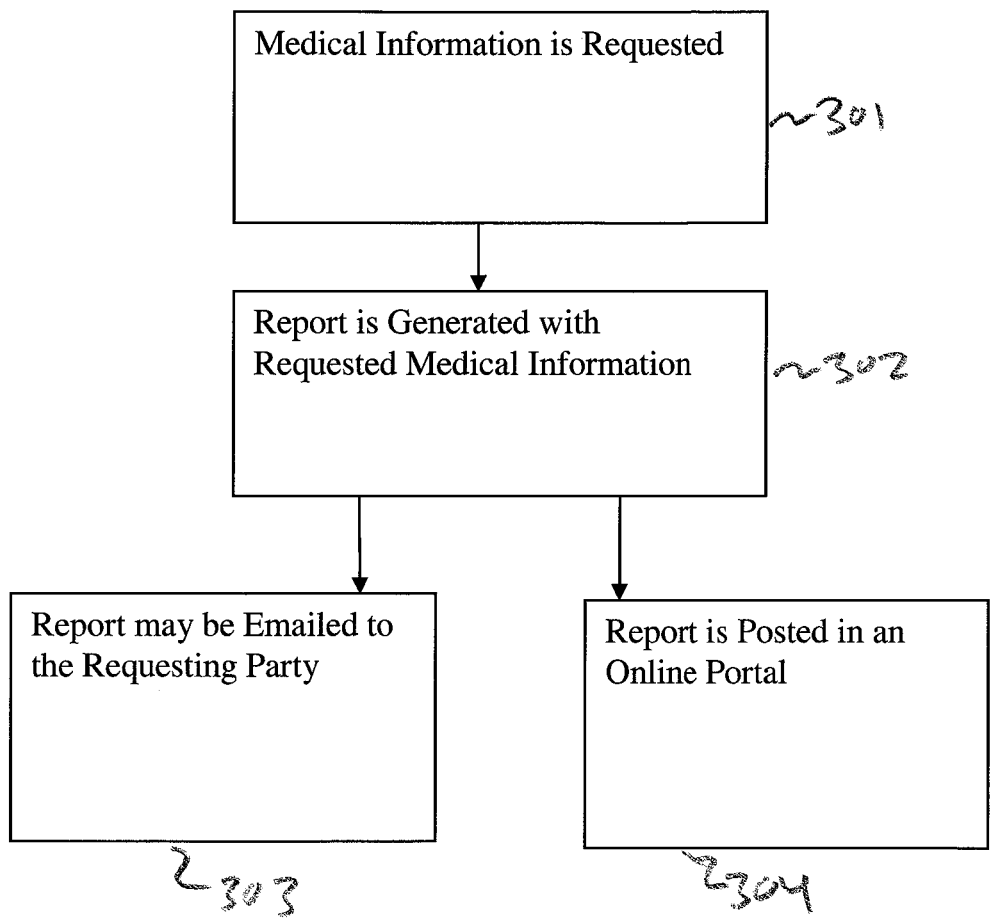
FIG. 3 is a flow chart showing the system and method of the present invention in which medical information is requested.

With reference to FIG. 3, a flow chart showing the system and method of the present invention in which medical information is requested is illustrated. A medical information report may be requested for a group member either by the group member or by a group record administrator, a records custodian and/or an authenticated medical provider 301. When requested, a report is generated with the requested medical information for the group member 302. The report may be emailed to the party requesting the information preferably using a HIPAA secure email service 303. The report may also be posted in an online portal that is accessible by the requesting party by using a secure link provided by the service provider 304. The portal may have a time limit for access placed thereon.

Figure 4:
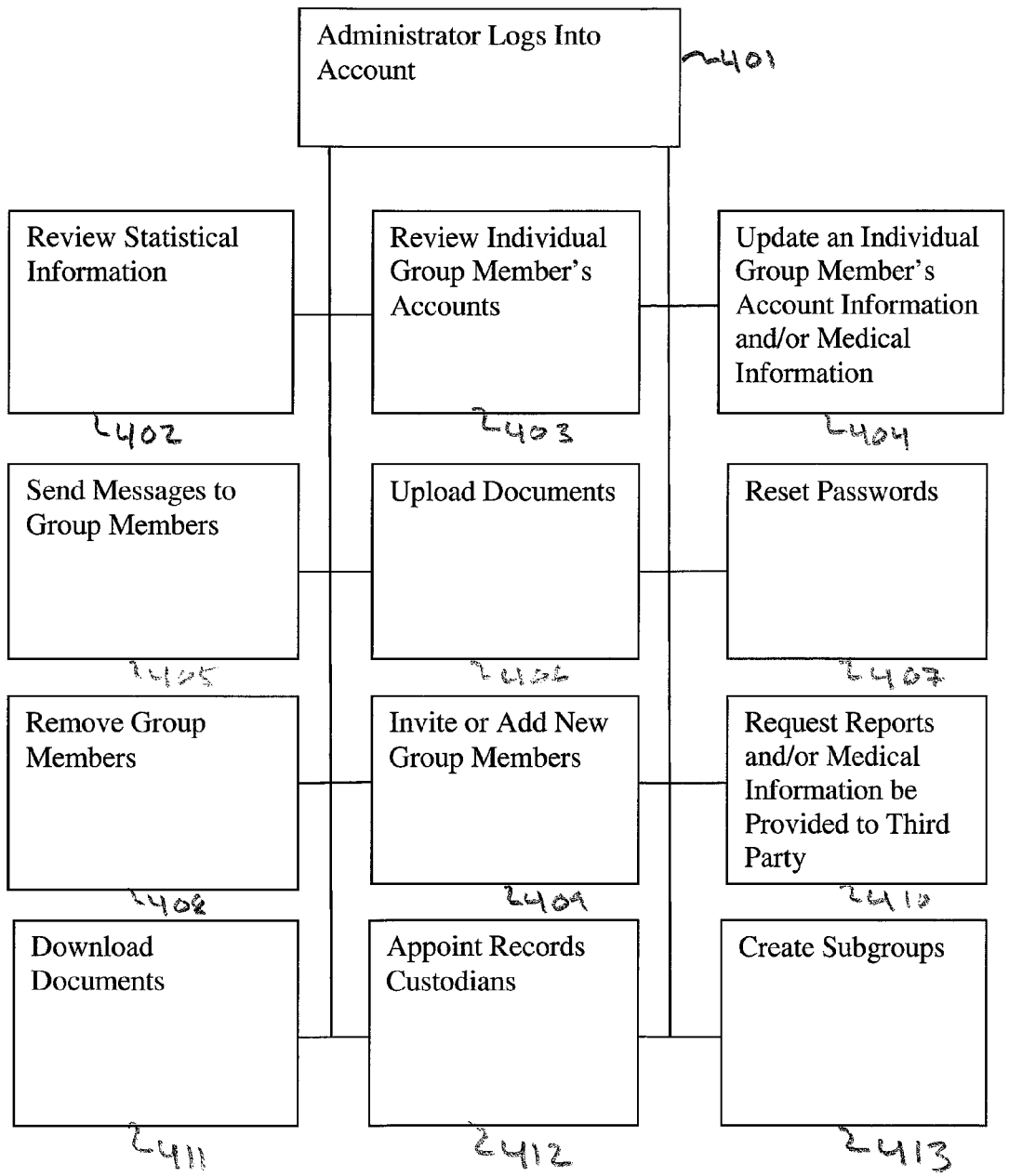
FIG. 4 is a block diagram showing administrative options for a group records administrator using the system and method of the present invention.

With reference to FIG. 4, a block diagram showing administrative options for a group records administrator using the system and method of the present invention is illustrated. After the group records administrator creates an account and a group database, as illustrated in FIG. 1, the group records administrator may log into the account 401 to perform a plurality of tasks including reviewing statistical information 402. Statistical information may include number of group members enrolled, completion of forms (such as consent forms and permission forms) and so forth. For example, such forms may be electronically signed by a parent and then saved in the database to be reviewed and/or accessed at alter time by a group records administrator. Physical copies of signed forms may also be digitized and then saved in the database.

The group records administrator may also review individual group member's accounts 403 to determine completeness of records, update an individual group member's account information or medical information 404 send messages to group members 405, upload documents 406 (such as permission forms), reset passwords 407, remove group members 408, invite or add new group members 409, request reports and/or medical information be provided to third parties 410 (such as medical providers), download documents 411, appoint records custodians 412, create subgroups 413 and so forth. For example a school principal may be a group records administrator. The principal may appoint assistant principals as records custodians who have total access to the group database or limited access or the principal may appoint a coach as records custodian of a subgroup of group members comprising a school sports team. Therefore, the coach will have access to the teams medical information if a medical emergency arises during a sporting event at the school or on the road.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

I claim:

1. A method for storing medical information of a group of individuals with a service provider and providing access to that medical information to a group records administrator comprising the steps of:
   a. a first individual providing the service provider with his or her contact information;
   b. the service provider reviewing the contact information and rendering a decision on whether to allow the individual to have an account;
   c. the first individual creating an account with a service provider over the internet;
   d. a group database being created for which the first individual is a records custodian; and
   e. one or more additional individuals creating accounts with the service provider and providing medical information to be saved in the group database.

2. The method of claim 1 further comprising steps of:
the service provider deciding to allow the first individual to have an account; and
the service provider creating an account and providing the first individual with a username and password.

3. The method of claim 1 further comprising steps of:
the service provider deciding to allow the one or more additional individuals to each have an account; and
the service provider creating an account and providing the one or more additional individuals each with a username and password.

4. The method of claim 1 further comprising a step of:
linking each of the one or more additional individual's accounts to a corresponding machine-readable medium.

5. The method of claim 1 further comprising a step of:
linking each of the one or more additional individual's accounts to a corresponding identification number.

6. The method of claim 1 further comprising a step of:
the first individual downloading software from the service provider onto an electronic device.

7. The method of claim 1 further comprising a step of:
the one or more additional individuals each downloading software from the service provider onto an electronic device.

8. The method of claim 1 further comprising a step of:
the one or more additional individuals providing one or more personal records to be saved in the group database.

9. A system for storing medical information of a group of individuals with a service provider and providing access to that medical information to a group records administrator comprising:
a first individual providing the service provider with his or her contact information;
the service provider reviewing the contact information and rendering a decision on whether to allow the first individual to have an account;
the first individual creating an account with a service provider over the internet;
a group database being created for which the first individual is a records custodian; and
accounts being created with the service provider for one or more additional individuals; and
the one or more additional individual's medical information being provided and saved in the group database.

10. The system of claim 9 further comprising:
a decision being made by the service provider to allow the first individual to have an account; and
an account being created by the service provider for the first individual.

11. The system of claim 9 further comprising:
a decision being made by the service provider to allow the one or more additional individuals to each have an account; and
accounts being created by the service provider for the one or more additional individuals.

12. The system of claim 9 further comprising:
the one or more additional individual's accounts being linked to a corresponding machine-readable medium.

13. The system of claim 9 further comprising:
the one or more additional individual's accounts being linked to a corresponding identification number.

14. The system of claim 9 further comprising:
software being downloaded by the first individual from the service provider onto an electronic device.

15. The system of claim 9 further comprising:
software being downloaded by the one or more additional individuals from the service provider onto an electronic device.

16. The system of claim 9 further comprising:
one or more personal records being provided to be saved in the group database.

17. A system for storing personal records of a group of individuals with a service provider and providing access to the personal records to a group records administrator comprising:
a first individual providing the service provider with his or her contact information;
the service provider reviewing the contact information and rendering a decision on whether to allow the first individual to have an account;
the first individual creating an account with a service provider over the internet;
a group database being created for which the first individual is a records custodian; and
accounts being created with the service provider for one or more additional individuals; and
the one or more additional individual's personal records being provided and saved in the group database.

18. The system of claim 17 further comprising:
a decision being made by the service provider to allow the first individual to have an account; and
an account being created by the service provider for the first individual.

19. The system of claim 17 further comprising:
a decision being made by the service provider to allow the one or more additional individuals to each have an account; and
accounts being created by the service provider for the one or more additional individuals.

\* \* \* \* \*